United States Patent [19]

Chu et al.

[11] Patent Number: 5,428,024
[45] Date of Patent: Jun. 27, 1995

[54] HIGH CONCENTRATION HOMOGENIZED COLLAGEN COMPOSITIONS

[75] Inventors: George Chu, Cupertino; Brenda Trobaugh, Santa Cruz; Prema Rao, Los Gatos, all of Calif.

[73] Assignee: Collagen Corporation, Palo Alto, Calif.

[21] Appl. No.: 229,859

[22] Filed: Apr. 19, 1994

Related U.S. Application Data

[63] Continuation of Ser. No. 843,770, Feb. 28, 1992, abandoned.

[51] Int. Cl.[6] .................... C08L 89/06; A61L 15/00; A61F 2/00; A61B 19/00
[52] U.S. Cl. ........................................ 514/21; 530/356
[58] Field of Search ........................ 530/356; 514/21

[56] References Cited

U.S. PATENT DOCUMENTS

| | | | |
|---|---|---|---|
| 3,949,073 | 4/1976 | Daniels et al. | 514/2 |
| 4,424,208 | 1/1984 | Wallace et al. | 530/356 |
| 4,582,640 | 4/1986 | Smestad et al. | 530/356 |
| 4,803,075 | 2/1989 | Wallace et al. | 530/356 |

OTHER PUBLICATIONS

McPherson et al. (1988) J. Dermatol. Surg. Oncol. 14 (suppl 1) 7 Jul.

*Primary Examiner*—Howard E. Schain
*Assistant Examiner*—Lynn Touzeau
*Attorney, Agent, or Firm*—Townsend and Townsend Khourie and Crew

[57] ABSTRACT

High concentration collagen compositions having improved persistence when administered for soft tissue augmentation are prepared from both cross-linked and non-cross-linked collagen starting materials. Suspensions of the starting materials are subjected to vigorous mechanical disruption to reduce the average collagen fiber size to below a threshold level which enhances the injectability of the composition. Thus, both enhanced injectability and enhanced persistence may be achieved using the same formulations.

6 Claims, 16 Drawing Sheets

- NON-HOMOGENIZED NON-CROSSLINKED COLLAGEN (35 MG/ML)
- NON-HOMOGENIZED NON-CROSSLINKED COLLAGEN (65 MG/ML)
- HOMOGENIZED NON-CROSSLINKED COLLAGEN (90 MG/ML)
- ▲ NON-HOMOGENIZED CROSSLINKED COLLAGEN (35 MG/ML)
- + HOMOGENIZED CROSSLINKED COLLAGEN (65 MG/ML)

HIGH CONCENTRATION HOMOGENIZED COLLAGEN COMPOSITIONS

This is a Continuation Ser. No. 07/843,770, filed Feb. 28, 1992, now abandoned.

BACKGROUND OF THE INVENTION

1. Field of the Invention

The present invention relates generally to compositions, methods for treatment, and methods for preparation of injectable collagen implant materials for soft tissue augmentation. More particularly, the present invention relates to high concentration collagen compositions that have been homogenized to enhance injectability.

The use of both cross-linked and non-cross-linked collagen compositions for soft tissue repair and augmentation is known. The preparation and use of non-cross-linked collagen compositions is described in U.S. Pat. No. 3,949,073, the disclosure of which is fully incorporated herein by reference. A commercial product incorporating non-cross-linked collagen at a concentration of 65 mg/ml is available from Collagen Corporation, Palo Alto, Calif., under the tradename Zyderm II. The preparation and use of cross-linked collagen compositions is described in U.S. Pat. No. 4,582,640, the disclosure of which is fully incorporated herein by reference. A commercial product incorporating cross-linked collagen at a concentration of 35 mg/ml is available from Collagen Corporation, Palo Alto, Calif., under the tradename Zyplast.

The use of both cross-linked and non-cross-linked collagen compositions for soft tissue repair and augmentation has been limited by a lack of "persistence," where persistence is defined as the tendency for the implanted collagen to form a cohesive mass and resist migration from an injection site. Previous injectable collagen compositions have also suffered from syneresis where the liquid component of the composition (typically a gel) separates during or after injection, resulting in a non-uniform consistency in the implant.

One approach for improving persistence and reducing syneresis might be to increase the collagen concentration in the composition used for soft tissue augmentation. Heretofore, the use of high concentration collagen compositions has been shown to be ineffective due to the difficulty in introducing the composition to the treatment site. Most commonly, collagen compositions are introduced as aqueous suspensions through a fine gauge needle to the tissue site of interest. Injection of high concentration collagen compositions is problematic. The use has been further discouraged by a perception that implants formed from high concentration collagens will calcify and harden over time. Hardened collagen implants are generally unacceptable for soft tissue implantation. For these reasons, any benefits which may derive from the use of high concentration collagen compositions remain speculative.

It would thus be desirable to provide improved collagen compositions, improved methods for preparing collagen compositions, and improved methods for therapeutically introducing such collagen compositions to a treatment site of interest. In particular, it would be desirable to provide collagen compositions having enhanced persistence after being introduced in vivo to a soft tissue treatment site within a patient. Even more particularly, it would be desirable to provide compositions having high collagen concentrations which remain readily injectable so that they can be introduced using fine gauge needles to the soft tissue site. In addition to the improved persistence, the collagen composition should be stable, i.e., undergo no significant changes (such as syneresis) in situ; be tough and elastic, i.e., be capable of bearing loads without undergoing excessive or permanent deformation; be non-toxic and well-tolerated by the body, i.e., produce no or tolerable levels of immune and inflammatory response; and be intrudable, i.e., form a relatively dispersed, irregular-shaped mass within the tissue where it has been introduced. It will be appreciated, of course, that the compositions and methods of the present invention while meeting at least some of these objectives, will not necessarily meet all of these objectives in every embodiment.

2. Description of the Background Art

U.S. Pat. Nos. 3,949,073 and 4,582,640, have been described above. U.S. Pat. No. 4,803,075, describes injectable cross-linked collagen compositions which are combined with a fluid lubricant to enhance intrudability. U.S. Pat. No. 4,424,208, describes a collagen composition including cross-linked collagen and reconstituted collagen fibers having enhanced persistence but limited extrusion and intrusion properties. U.S. Pat. No. 4,582,640, teaches that injectability of low concentration collagen compositions can be enhanced by forcing a suspension of the collagen fibers through a screen of defined pore size. It is suggested that the screen breaks up fibrillar aggregates that may be in the suspension to achieve a more uniform fiber size distribution. McPherson et al. (1988) J. Dermatol. Surg. Oncol. 14 (Suppl. 1) 7, describes improved persistence with non-homogenized 65 mg/ml non-cross-linked collagen (Zyderm II).

SUMMARY OF THE INVENTION

High concentration collagen compositions having improved in vivo persistence and reduced syneresis are prepared by vigorous homogenization of a suspension of fibrillar collagen to reduce the average collagen particle size in order to enhance injectability. Such compositions will have reduced viscosities and may be readily injected through a fine gauge needle, such as 25 gauge or smaller (i.e., higher gauge) to a soft tissue site for augmentation according to a method of the present invention. Surprisingly, the reduced collagen particle size and reduced viscosity may be achieved without adversely impacting other desirable implant characteristics, such as stability, toughness, elasticity, intrudability, and the like. Moreover, such compositions do not exhibit substantial calcification or hardening after implementation, making them suitable for said tissue implantation.

Compositions according to the present invention comprise soluble collagen obtained from an animal source, including both cross-linked collagen fibers and non-cross-linked collagen fibers. Suspensions of either the cross-linked or non-cross-linked collagen fibers will typically have an initial average fiber particle area in the range from about 1000 $\mu m^2$ to 10,000 $\mu m^2$ (for non-cross-linked collagens) and in the range from 10,000 $\mu m^2$ to 100,000 $\mu m^2$ (for cross-linked collagens). According to the method of preparation of the present invention, such suspensions are vigorously mechanically disrupted to reduce the average particle fiber size by at least 25% and preferably 50% for non-cross-linked collagens and by at least 50% and preferably 75% for cross-linked collagens. A preferred mechanical disrupting step comprises homogenization of the suspension using a cavitation homogenizer where the suspension is pressurized and subjected to intense cavitation forces. Non-cross-linked collagen concentrations will be greater than 65 mg/ml, preferably being from 65 mg/ml to 150 mg/ml, while cross-linked collagen concentrations will be greater than 35 mg/ml, preferably being from 35 mg/ml to 90 mg/ml.

DESCRIPTION OF THE SPECIFIC EMBODIMENTS

Figure 1:
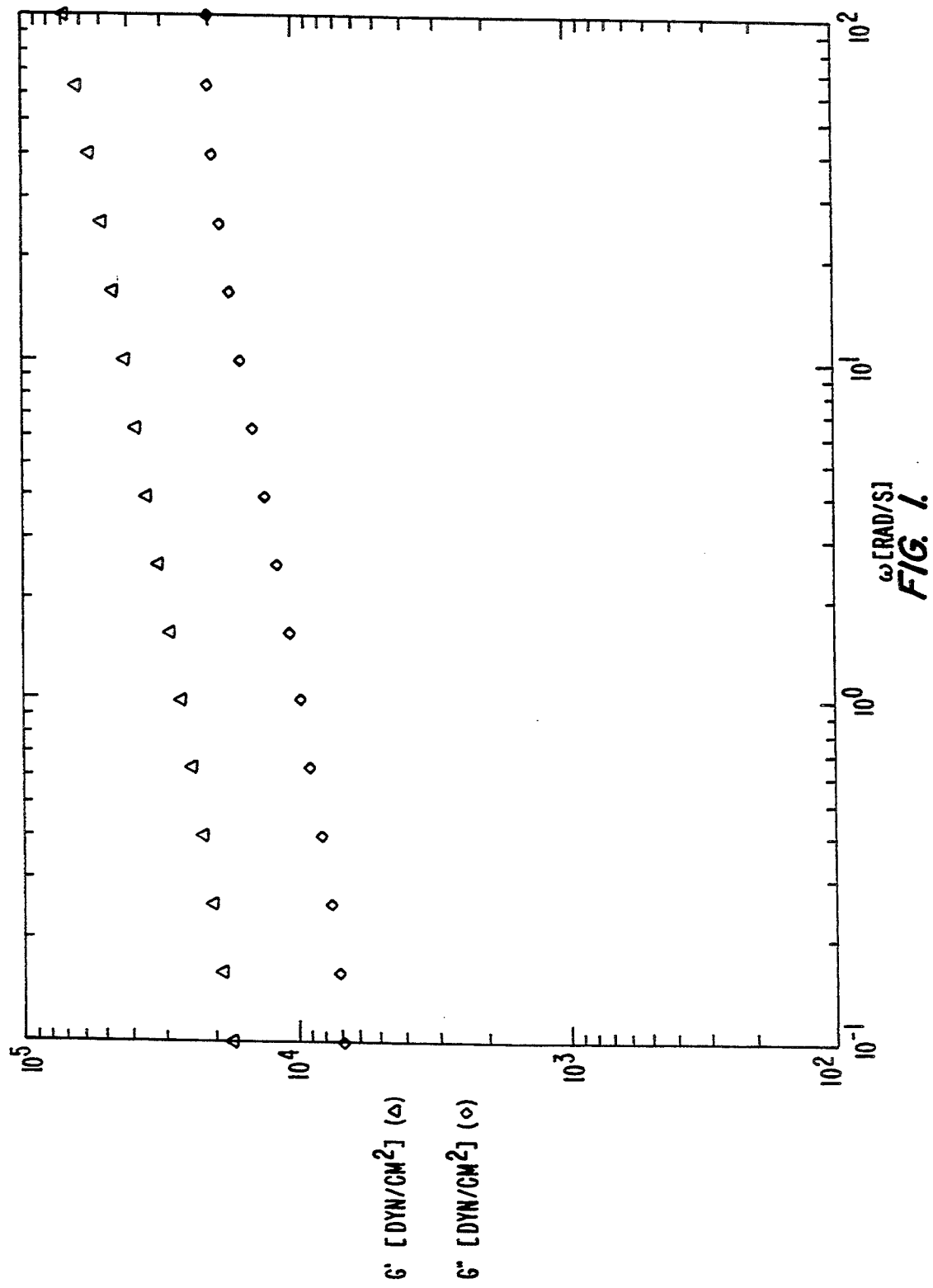
FIGS. 1-3 graphically illustrate frequencing sweep measurements made on non-homogenized non-crosslinked and homogenized non-crosslinked materials prepared as described in the Experimental section hereinafter.

According to the present invention, improved solubilized collagen compositions which are particularly useful for in vivo soft tissue augmentation are obtained by homogenization of certain high collagen concentration starting materials, where homogenization reduces the collagen fiber size within the resulting collagen composition compared to that of corresponding non-homogenized composition. The homogenized collagen compositions of the present invention are found to have improved injectability, improved persistence, and reduced syneresis, when used for soft tissue augmentation. Improved injectability is largely a matter of improved rheological characteristics such as reduced effective viscosity, with the compositions of the present invention usually having a reduced non-Newtonian viscosity profiles as described further in the experimental section hereinafter.

Although the compositions of the present invention are particularly suitable for soft tissue repair and augmentation by injection, they will also be useful for repair of bone, cartilage, and other body structures. The compositions may also be introduced by techniques other than injection and by injection through large bore needles.

Persistence is defined as the tendency for the collagen implant (which is formed by injection of the collagen compositions) to remain as a cohesive mass and to resist migration from the injection site. Persistence may be measured experimentally in an animal model, as described in detail in the Experimental section hereinafter.

The collagen fiber area in the compositions of the present invention will be reduced by at least 25% and preferably by at least 50% in the case of non-cross-linked collagen compositions (as described below) and will be reduced by at least 50% and preferably by at least 75% in the case of cross-linked collagen compositions (as described below). Collagen fiber area may be measured microscopically using an image analyzer, as described in detail in the Experimental section hereinafter.

The collagen concentration in the compositions of the present invention will depend on the nature of the collagen fiber. Cross-linked collagen fibers, prepared as described below, will be present in the compositions at a concentration of greater than 35 mg/ml, usually being in the range from about 35 mg/ml to 90 mg/ml, preferably being in the range from about 50 mg/ml to 75 mg/ml. For non-cross-linked collagen compositions, the collagen concentration will be greater than 65 mg/ml, usually being in the range from about 65 mg/ml to 150 mg/ml, preferably being in the range from about 80 mg/ml to 120 mg/ml.

The collagen starting materials may be low concentration cross-linked or non-cross-linked collagen suspensions prepared by conventional methods. The low concentration collagen starting materials are then subjected to concentration, typically by centrifugation, and mechanical disruption to reduce particle size and viscosity. The collagen fiber size in the low concentration starting materials will usually be greater than 1000 $\mu m^2$, usually being in the range from about 500 $\mu m^2$ to 4000 $\mu m^2$. The particle sizes in the concentrated compositions (prior to homogenization) will be increased, with initial average particle sizes for the non-cross-linked collagen being from about 1000 $\mu m^2$ to 10,000 $\mu m^2$ and initial average particle sizes for the cross-linked collagen being from about 10,000 $\mu m^2$ to 100,000 $\mu m^2$. These particle sizes may be determined using the method described in the Experimental section hereinafter.

The collagen used as a starting material in the invention may be derived from collagen collected from any number of mammalian sources, such as bovine or porcine corium and human placenta. Bovine or porcine corium will usually be employed because of easier availability and lower cost.

The first step in making the high concentration collagen suspension is to prepare atelopeptide collagen in solution from the corium. The animal skin is softened by soaking it in a mild acid and then scraping it to remove hair, epidermis, and fat. The depilated skin is then soaked again in mild acid and then comminuted by grinding, mincing, milling or like physical treatment. The comminution prepares the skin for solubilization.

The comminuted tissue may be solubilized under non-denaturing conditions by dispersing it in an aqueous medium and digesting it with a proteolytic enzyme other than a collagenase, preferably an enzyme that is active at acidic pHs. Dilute acid solutions at low temperatures will normally be used to avoid denaturation. Mineral acids such as HCl or carboxylic acids such as acetic, malonic or lactic acids may be used. The pH will normally be in the range of about 1.5 to 5, depending on the enzyme used, and the temperature about 5° C. to 25° C.

After the tissue is dispersed, the enzyme is added and the mixture is incubated to permit the enzyme to digest the telopeptide and other solubilizable components of the tissue. Enzymes that attack the telopeptide portion of the collagen while not denaturing the helical portion are used. Examples of such enzymes are pepsin and papain. Pepsin is preferred because it is relatively easily deactivated and removed from the solubilized collagen. The enzyme concentration will usually be in the range of about 0.1% to 10% by weight based on the collagen. The incubation period will typically vary from about two days to two weeks. The progress of the solubilization may be monitored by determining the viscosity of the solution. Once the viscosity reaches a substantially constant level, the solubilization is complete. At this point, the enzyme is deactivated (denatured) and removed. The enzyme may be deactivated by raising the pH of the solution to at least about 7 by adding an alkaline material such as sodium hydroxide.

After the enzyme has been denatured, the solution is treated to remove denatured enzyme and the portions of the tissue that were not digested during the solubilization. Various dialysis, sedimentation, and filtration techniques may be used to effect such removal. See U.S. Pat. Nos. 3,949,073 col. 3, lines 10–22 and 4,140,537 col. 5, line 48 to col. 6, line 34, which disclosures are incorporated herein by reference.

To prepare a cross-linked collagen starting material, the atelopeptide collagen is reconstituted from solution. The reconstitution is preferably done by neutralizing the solution at reduced temperatures, preferably about 10° C. to 25° C. The ionic strength of the neutralized solution is preferably hypotonic relative to physiological conditions. Ionic strengths in the range of about 0.03 to about 0.1, will typically be used. The neutralization involves raising the pH of the solution by adding an appropriate base or buffer, such as $Na_2HPO_4$ or NaOH, to a level at which the collagen in solution reaggregates into fibrils. Fiber formation occurs under these conditions at pHs in the range of about 4.9 and about 10.0. The final pH is preferably in the range of about 5 and 8. The duration of the fibril formation step will normally be in the range of about ½ to about 18 hr.

The resulting reconstituted atelopeptide fibrous collagen gel suspension is then cross-linked using various methods known in the art, such as heat treatment or irradiation. Chemical cross-linking agents that form covalent bonds with collagen can also be used. Usually the agent will be polyfunctional or bifunctional. The cross-linking conditions are such as to produce a covalently cross-linked collagen that may be formulated as an injectable fluid and that provides an implant that has improved persistence relative to an implant made from a comparable formulation of non-cross-linked fibrous atelopeptide collagen. When this degree of cross-linking has been reached, the cross-linking reaction is optionally quenched by adding a quenching agent. The quenching agent forms a water soluble adduct with the cross-linking agent. The concentration of collagen in the suspension must be sufficiently low to cause the cross-linking to be substantially intrafibrillar rather than interfibrillar. With intrafibrillar cross-linking the collagen particles can still flow, whereas at high collagen concentrations there is significant interparticle cross-linking and the product becomes solid or too viscous to flow. The collagen concentration at the time of cross-linking will usually be in the range of 0.1 to 10 mg/ml.

Aldehydes are preferred cross-linking agents. Examples of aldehydes that may be used to cross-link the collagen are formaldehyde, glutaraldehyde, acetaldehyde, glyoxal pyruvic aldehyde, and dialdehyde starch. Preferred methods for cross-linking collagen with glutaraldehyde are described in U.S. Pat. Nos. 4,582,640 and 4,642,117, the disclosures of which are incorporated herein by reference.

Both the cross-linked and non-cross-linked collagen starting materials will be subjected to vigorous mechanical disruption to reduce the average collagen particle size by two to ten-fold. Such mechanical disruption may be achieved by a high energy disruption or comminution device, such as the HC-5000 Laboratory Homogenizer available from Microfluidics Corporation, Newton, Mass. Other suitable homogenizers include the Gaulin HS-2 Hydroshear, the Brinkmann Homogenizer, and the Virtis Homogenizer.

The ionic strength of the aqueous suspensions of homogenized, high concentration collagen will typically be adjusted to isotonicity. A local anesthetic, such as lidocaine, may be added to the final formulation to reduce local pain upon injection. The suspension is then loaded into syringes fitted with a No. 25 gauge or smaller bore needle for injection. The above described steps in the process for preparing the novel injectable cross-linked collagen are preferably carried out in sterile conditions using sterile materials. Optionally, the homogenized compositions may be mixed, e.g., by syringe-syringe mixing, prior to or in combination with loading into the injection syringe. Such mixing has been found to further enhance injectability, particularly of the cross-linked compositions.

The term "injectable" means that the compositions can be dispensed from syringes under normal conditions under normal manual pressure without substantial spiking. The compositions will be injectable through at least a 20 gauge needle, preferably being injectable through 22 gauge needles, more preferably being injectable through 25 gauge needles, and even more preferably being injectable through 30 gauge needles and smaller.

The above described collagen implant material may be injected intradermally or subcutaneously to augment soft tissue, to repair or correct congenital anomalies, acquired defects or cosmetic defects. Examples of such conditions are congenital anomalies such as hemifacial microsomia, malar and zygomatic hypoplasia, unilateral mammary hypoplasia, pectus excavatum, pectoralis agenesis (Poland's anomaly) and velopharyngeal incompetence secondary to cleft palate repair or submucous cleft palate (as a retropharyngeal implant); acquired defects (post traumatic, post surgical, post infectious) such as depressed scars, subcutaneous atrophy (e.g., secondary to discoid lupis erythematosis), keratotic lesions, enophthalmos in the unucleated eye (also superior sulcus syndrome), ache pitting of the face, linear scleroderma with subcutaneous atrophy, saddlenose deformity, Romberg's disease and unilateral vocal cord paralysis; and cosmetic defects such as glabellar frown lines, deep nasolabial creases, circumoral geographical wrinkles, sunken cheeks, mammary hypoplasia, anal sphincter augmentation, and hemorrhoids. See in particular copending applications Ser. No. 07/843,124 and Ser. No. 07/843,379, the disclosures of which are incorporated herein by reference.

The following examples illustrate preparation of the collagen implant materials, the methods by which these materials are used, and the merits of implants made from these materials. These examples are not intended to limit the invention in any manner.

EXPERIMENTAL

1. Homogenized Non-crosslinked Collagen

A. Preparation

Vitrogen® 100 collagen-in-solution (CIS) was obtained from Celtrix Laboratories (Palo Alto, Calif.). Fibrous collagen was reconstituted from Vitrogen® 100 at 2.9 mg/ml by the addition of $Na_2HPO_4$ buffer. The mixture was stirred and allowed to incubate at 17° C. for approximately 17 hours. The slurry was centrifuged at 13,280×g. The protein concentration of the resulting pellet was estimated at 122 mg/ml.

The pellet was homogenized and the concentration adjusted to 90 mg/ml in $Na_2HPO_4$, NaCl, and lidocaine.

TABLE II

| | Force (Newtons) | | |
|---|---|---|---|
| | 90 mg/ml non-crosslinked collagen | | |
| Speed (mm/min) | non-homogenized | homogenized | 65 mg/ml non-homogenized, non-crosslinked collagen |
| 10 | 13 | 15 | 12.5 |
| 30 | 16 | 22 | 17 |
| 50 | 19 | 26 | 21 |
| 100 | 28 | 35 | 28 |

The homogenized material was extrudable through a 30-gauge needle.

Three samples were analyzed and found to have an average protein concentration of 86.6 mg/ml. Minimal concentration differences between the three samples indicated that the material was well homogenized.

The material was further homogenized in the HC-5000 homogenizer and collected after recirculation for 10 minutes.

B. Chemical Properties

The homogenized non-crosslinked collagen was tested for various chemical properties. The results are presented in Table I.

TABLE I

| Test | Results |
|---|---|
| pH | 7.1 |
| Protein Conc. | 87.8 mg/ml |
| Lidocaine Conc. | 2.5 mg/ml |
| Extrusion (27 ga. needle) | 25 N |
| DSC | 58° C. |
| % Denaturation | 4% |
| Residue on Ignition | 0.7% |
| % Alpha Band | 55% |
| Carbohydrate Conc. | 4 µg CHO/mg collagen |

C. Rheological Measurements

Rheological measurements were performed on the following materials;

1. 90 mg/ml non-homogenized non-crosslinked collagen.
2. 90 mg/ml homogenized non-crosslinked collagen.
3. 65 mg/ml non-homogenized non-crosslinked collagen.

Figure 2:
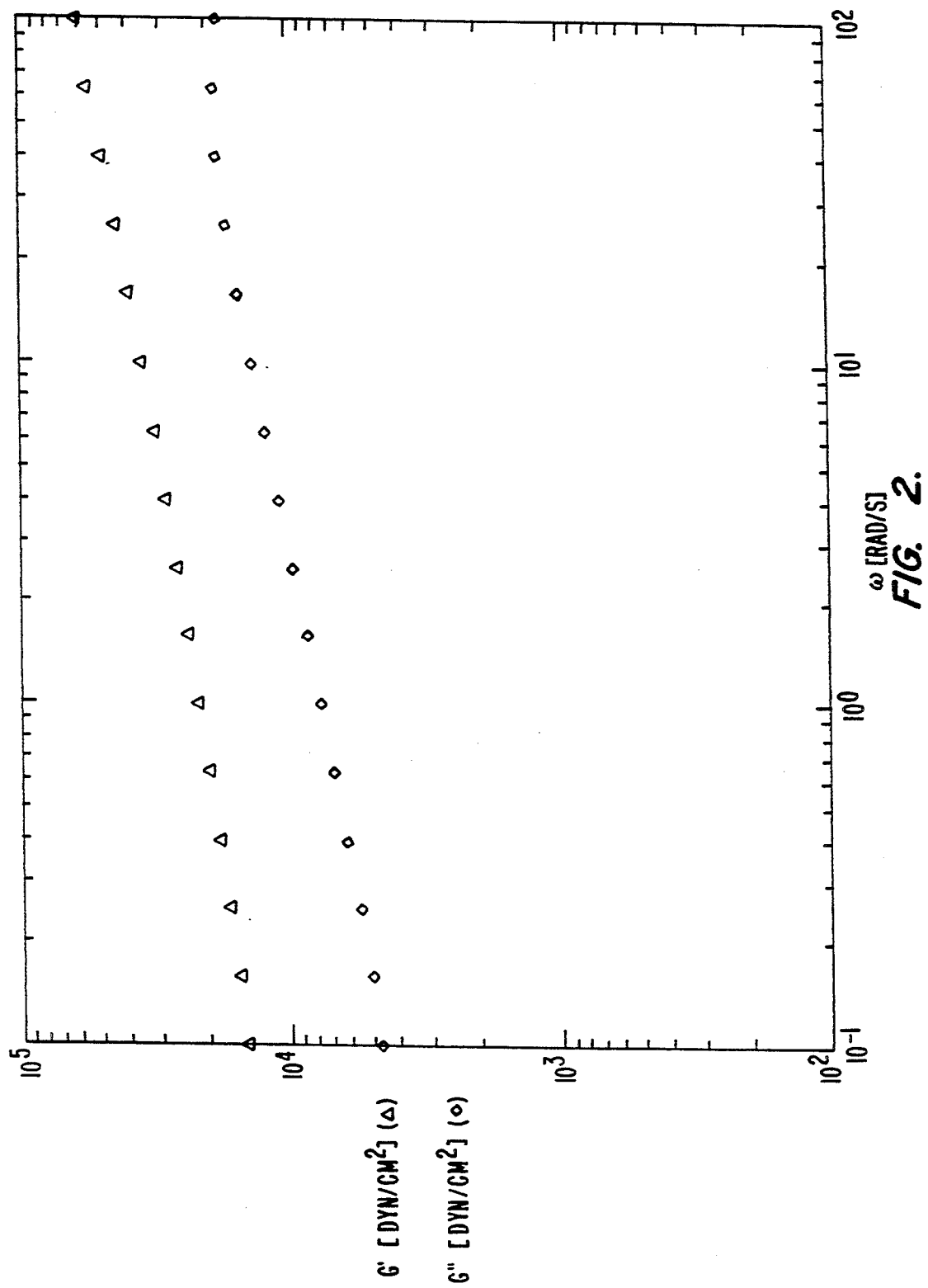
Figure 3:
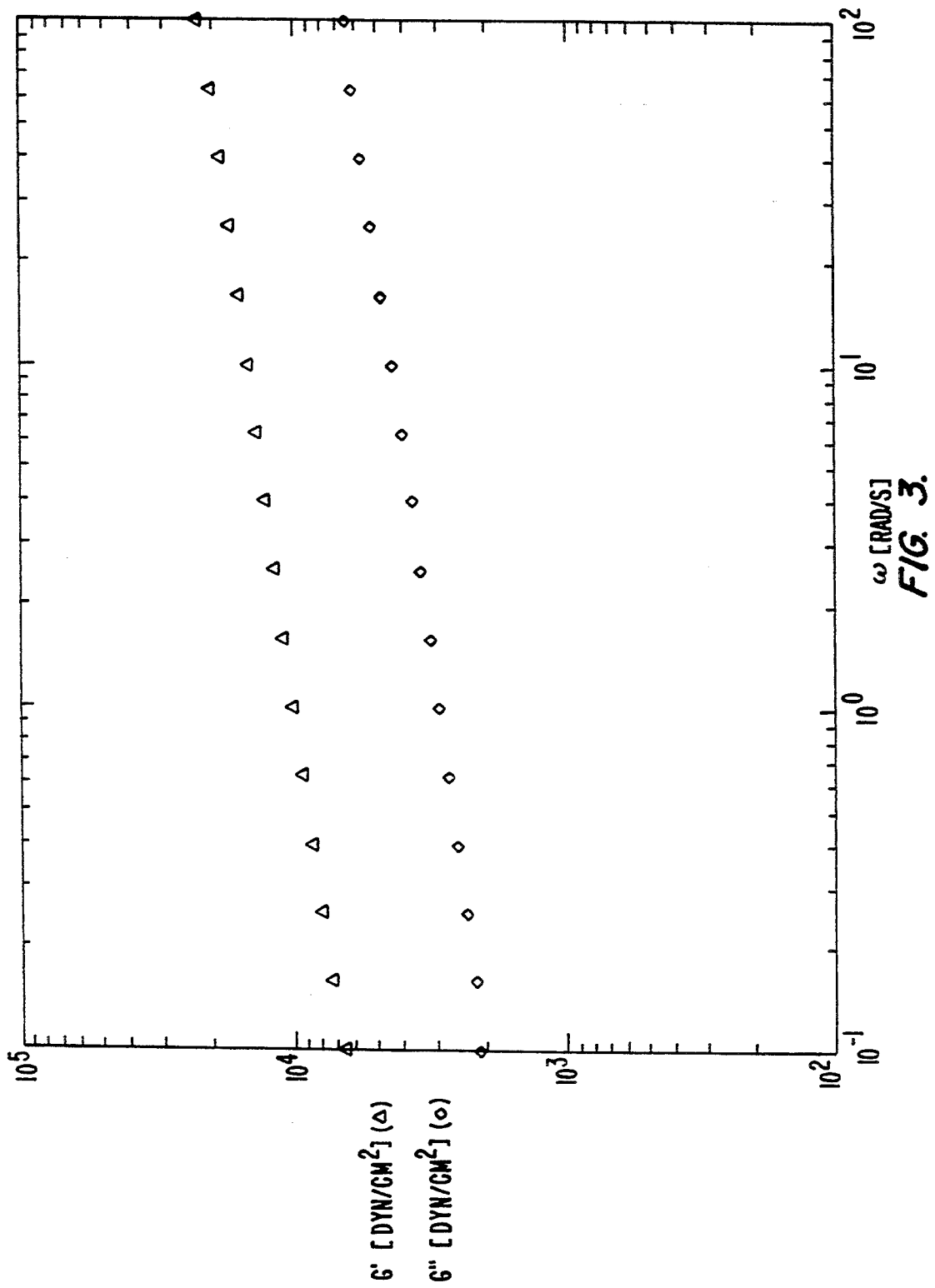
Figure 4:
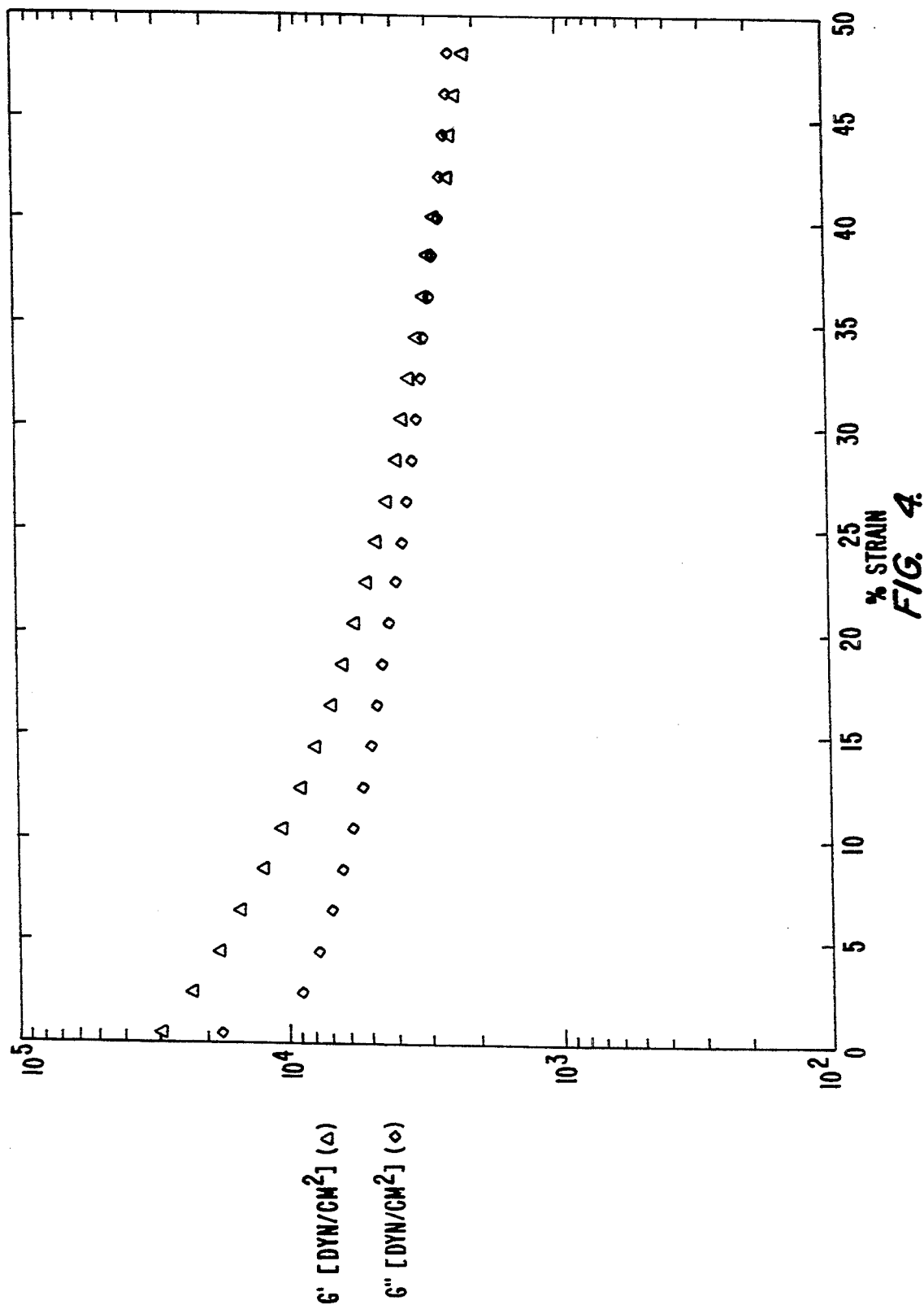
FIGS. 4-6 graphically illustrate strain sweep measurements made on non-homogenized non-crosslinked and homogenized non-crosslinked materials prepared as described in the Experimental section hereinafter.
Figure 5:
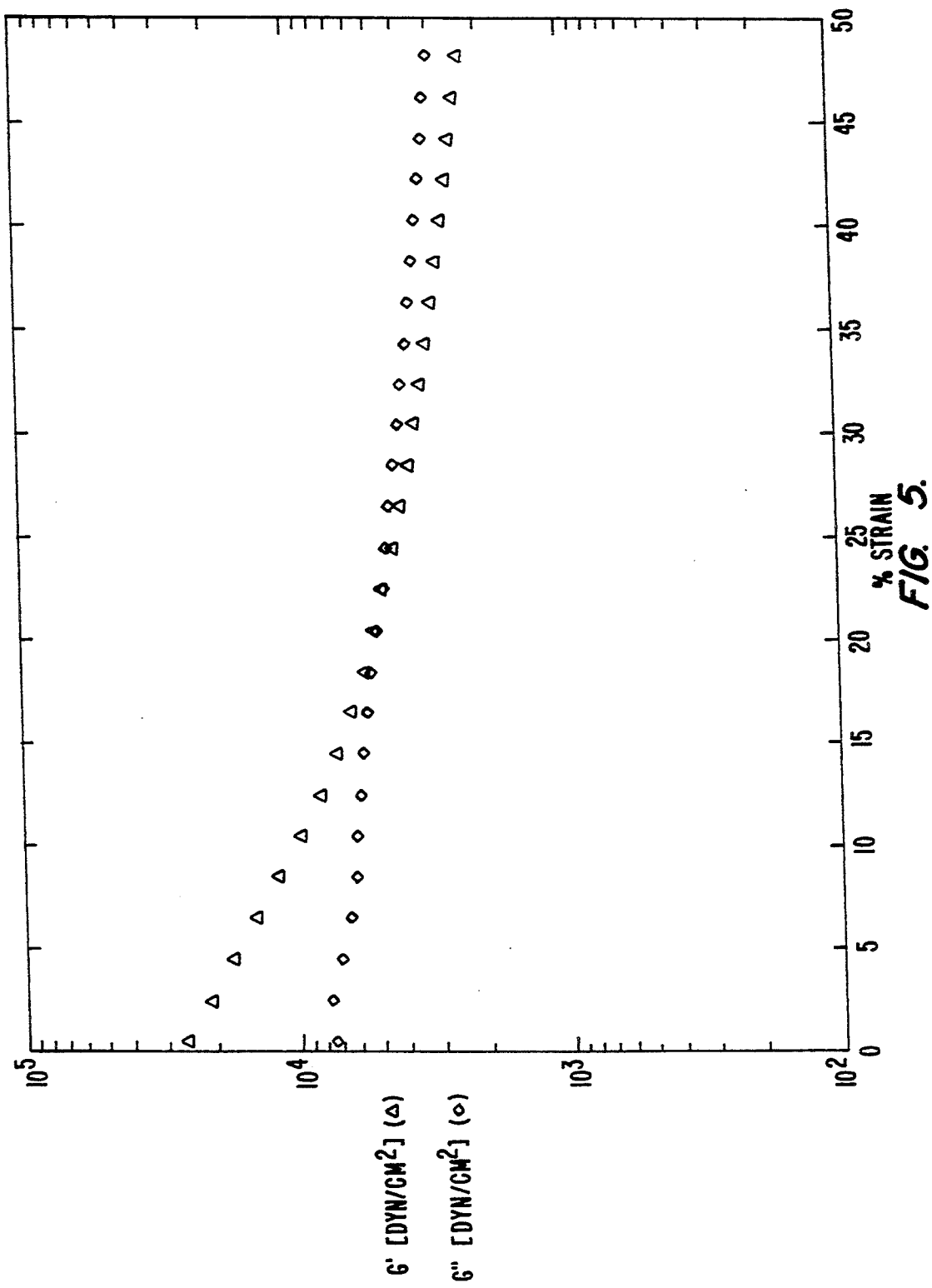
Figure 6:
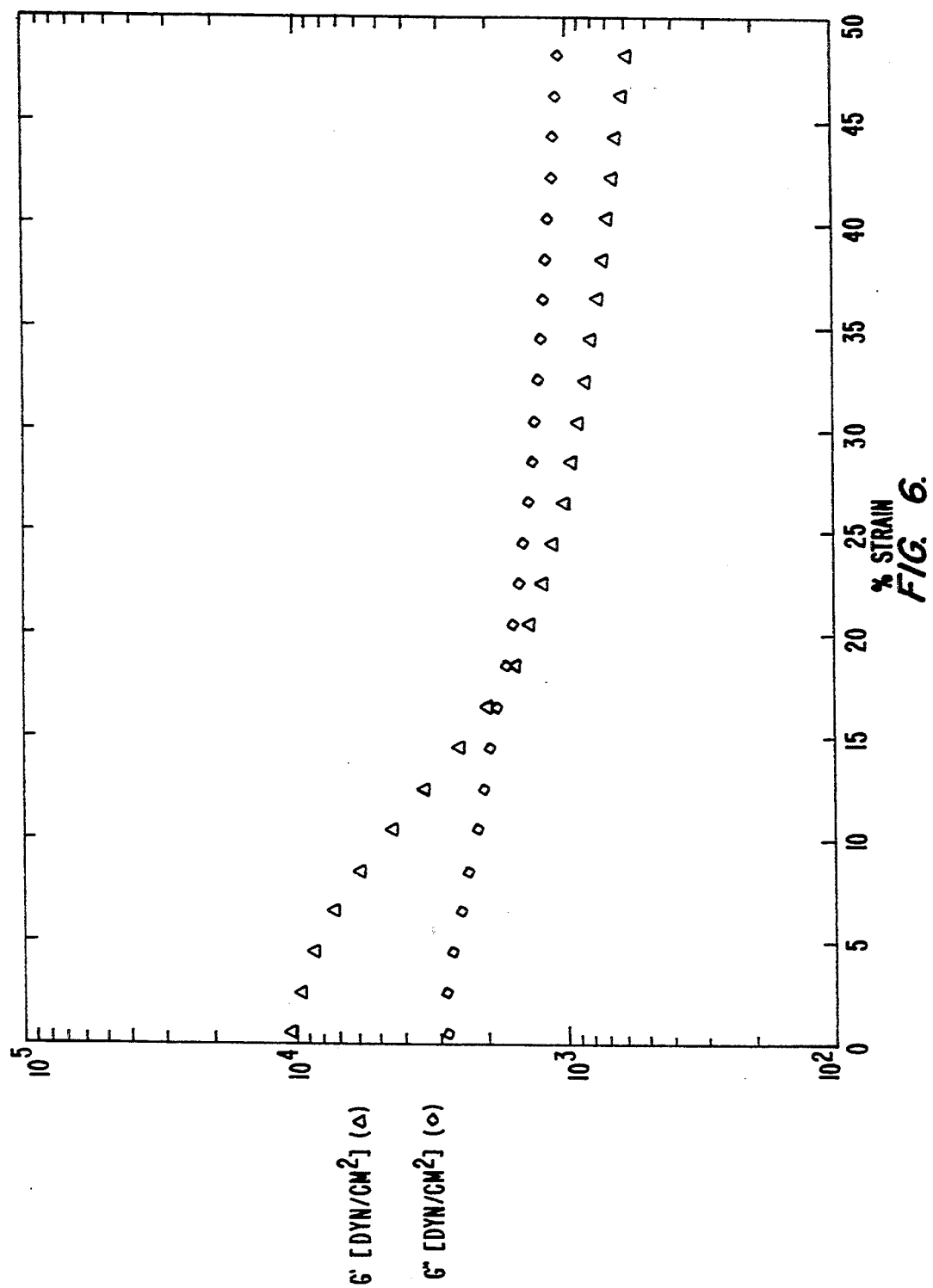
Figure 7:
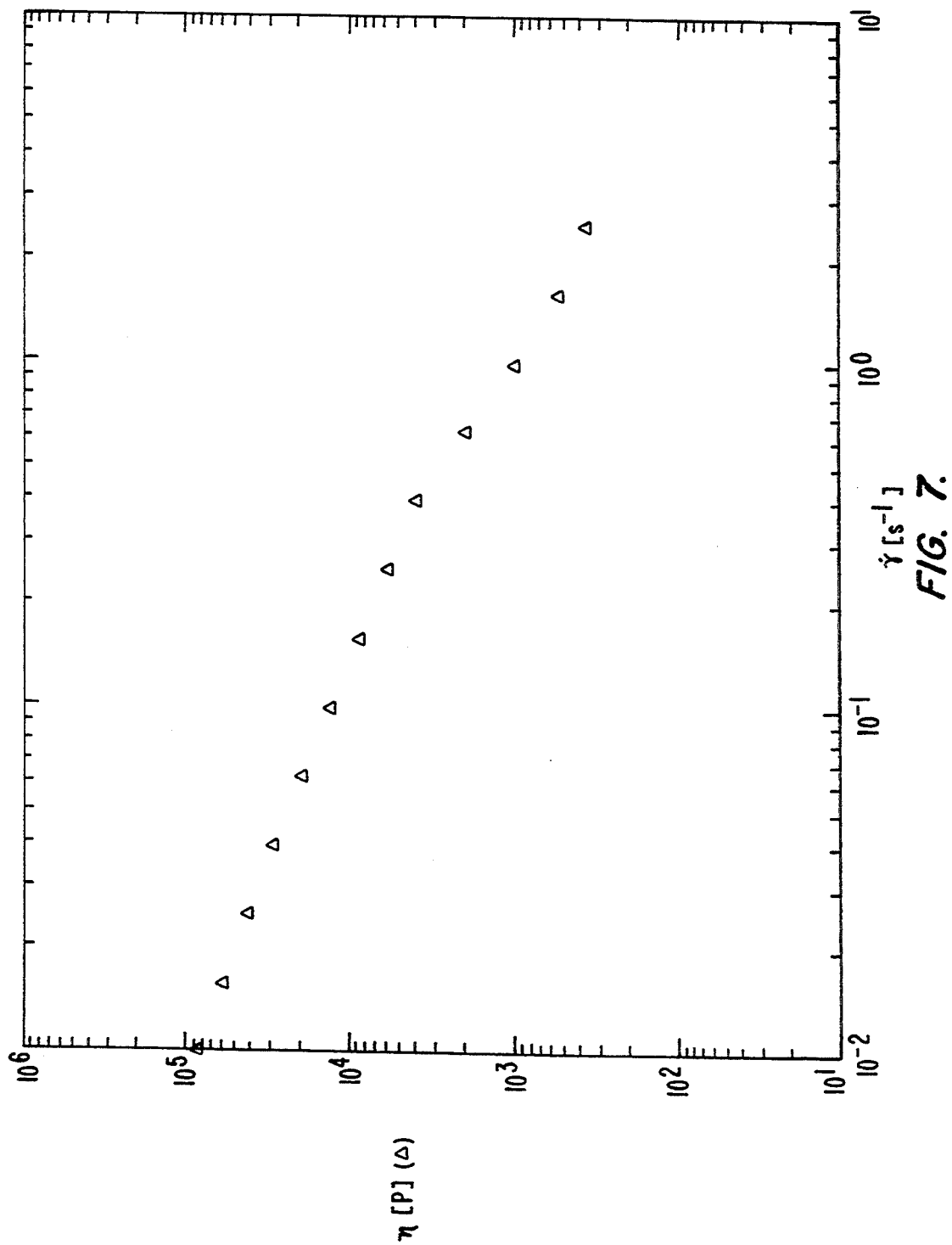
FIG. 7 graphically illustrates steady shear viscosity ($\eta$) as a function of shear rate ($\gamma$) for a homogenized, non-crosslinked collagen prepared as described in the Experimental section hereinafter.

The following measurements were performed using a Rheometrics Fluid Spectrometer (Rheometrics, Inc., Piscataway, N.J.) at 20° C.:

1. Frequency sweep at 1% strain (FIGS. 1, 2, and 3).
2. Strain sweep from 0.5 to 50% strain at 1 rad/sec (FIGS. 4, 5, and 6).
3. Steady shear viscosity versus shear rate (FIG. 7).

The results of these tests are shown in FIGS. 1 through 7.

The data indicate that the frequency and strain sweeps are very similar for all three materials. However, the 90 mg/ml homogenized non-crosslinked collagen appears to be slightly more consistent and homogeneous, with better flow properties, than the 65 mg/ml non-homogenized non-crosslinked collagen. The data also indicate that the 90 mg/ml homogenized non-crosslinked collagen has a higher viscosity and is slightly more shear-thinning (decrease in viscosity with increasing shear rate) than the 65 mg/ml non-homogenized non-crosslinked collagen.

D. Extrusion

Extrusion through a 30-gauge needle was measured for the three materials to verify sample homogeneity and to obtain force of extrusion speed data. Data are presented in Table II.

Good extrusion plateaus were obtained with all samples. The extrusion plateaus were uniform with few spikes, suggesting fairly homogeneous material. Extrusion forces required were similar for all three materials. The extrusion forces for the 90 mg/ml homogenized collage were slightly higher than for the 90 mg/ml non-homogenized collagen. This may be due to the face that different lots of material were tested.

E. Capillary Rheometry

Figure 8:
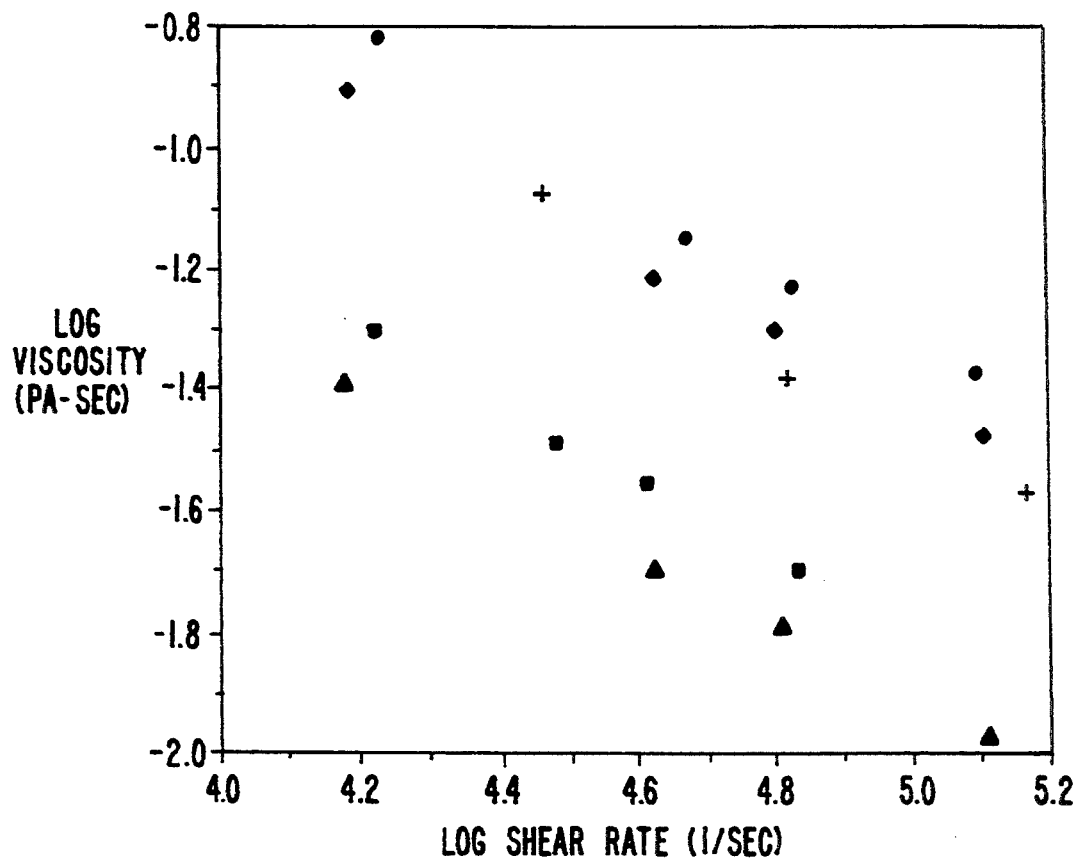
FIG. 8 graphically illustrates viscosity as a function of shear rate for non-homogenized non-crosslinked, homogenized non-crosslinked, non-homogenized crosslinked, and homogenized crosslinked materials prepared described in the Experimental section hereinafter.

Capillary rheometry measurements were performed on 90 mg/ml homogenized non-crosslinked collagen and 65 mg/ml non-homogenized non-crosslinked collagen to compare changes in material structure and flow rate. The capillary rheometry technique consisted of performing extrusions at multiple speeds through long narrow-gauge needles on an Instron Analyzer (Instron Corp., Canton, Mass.). Viscosity/shear rate values are then calculated from the extrusion speed data. Viscosity/shear rate data are shown in Table III and FIG. 8.

TABLE III

| Shear Rate (1/sec) | Viscosity (Pa-sec) |
|---|---|
| 90 mg/ml homogenized non-crosslinked collagen | |
| 17094.67 | 0.15194 |
| 47035.11 | 0.07146 |
| 67037.28 | 0.05926 |
| 125528.40 | 0.04260 |
| 65 mg/ml non-homogenized non-crosslinked collagen | |
| 15474.65 | 0.12342 |
| 42343.46 | 0.06134 |
| 63724.46 | 0.05035 |
| 127354.55 | 0.03359 |

Viscosity/shear rate data were similar for the two materials.

F. Fiber Size Distribution

Fiber size distribution was measured for the following three materials by image analysis using an Olympus Cue-2 Image analyzer (Olympus, Japan).

1. 90 mg/ml non-homogenized non-crosslinked collagen.
2. 90 mg/ml homogenized non-crosslinked collagen.
3. 65 mg/ml non-homogenized non-crosslinked collagen.

Fiber size distribution data are presented in Table IV.

TABLE IV

| | Minimum to Maximum Object Area ($\mu m^2$) | Mean object Area ($\mu m^2$) |
|---|---|---|
| 90 mg/ml non-crosslinked collagen | | |
| Non-homogenized | 34 to $1.42 \times 10^5$ | $4412 \pm 13557$ |
| Homogenized | 34 to $6.99 \times 10^4$ | $2353 \pm 6001$ |
| 65 mg/ml non-homogenized Non-crosslinked collagen | 34 to $2.35 \times 10^4$ | $1309 \pm 3087$ |

The data indicate that homogenization causes the fiber size to decrease by a factor of two. Fiber size of the 90 mg/ml homogenized collagen is similar to that of the lower concentration material. It also must be noted that variation in fiber size decreases following homogenization, indicating a more homogeneous material.

2. Homogenized Crosslinked Collagen

A. Preparation

Fibrous collagen was reconstituted from Vitrogen 100 at 2.9 mg/ml by the addition of $Na_2HPO_4$ buffer. The mixture was stirred and allowed to incubate at 19° C. for approximately 3 hours.

Crosslinking was effected by the addition of glutaraldehyde (300 ppm) to the precipiated fibrous collagen to obtain a final ratio of 12 mg glutaraldehyde per gram of collagen. The slurry was stirred and allowed to incubate for 20 hours at 20° C. The cross-linked slurry was centrifuged at $13,280 \times g$. The resulting material was estimated to have a collagen concentration of approximately 92 mg/ml.

The centrifugation pellet was then homogenized and the concentration adjusted to 65 mg/ml in $Na_2HPO_4$, NaCl, and lidocaine. The material was analyzed for protein concentration and found to be 65 mg/ml.

The partially homogenized material was then subjected to more vigorous homogenization in the HC-5000 homogenizer. The material was recirculated through the HC-5000 and periodically tested for extrudability. Following 1.5 hours of homogenization, the material was extrudable through a 30-gauge needle.

B. Chemical Properties

The homogenized crosslinked collagen was tested for various chemical properties. The results are presented in Table V.

TABLE V

| Test | Result |
|---|---|
| pH | 7.0 |
| Protein Concentration | 64.2 mg/ml |
| Free Glutaraldehyde | $1.6 \pm 0.1$ ppm |
| Lidocaine Concentration | 2.8 mg/ml |
| Extrusion (27-gauge needle) | 27 N |
| DSC | 71° C. |
| Carbohydrate Concentration | 2 $\mu$g CHO/mg collagen |

C. Rheological Measurements

Rheological measurements were performed on the following materials:

1. 65 mg/ml non-homogenized crosslinked collagen.
2. 65 mg/ml homogenized crosslinked collagen.
3. 35 mg/ml non-homogenized crosslinked collagen.

The following measurements were performed on a Rheometrics Fluid Spectrometer at 20° C.

Figure 9:
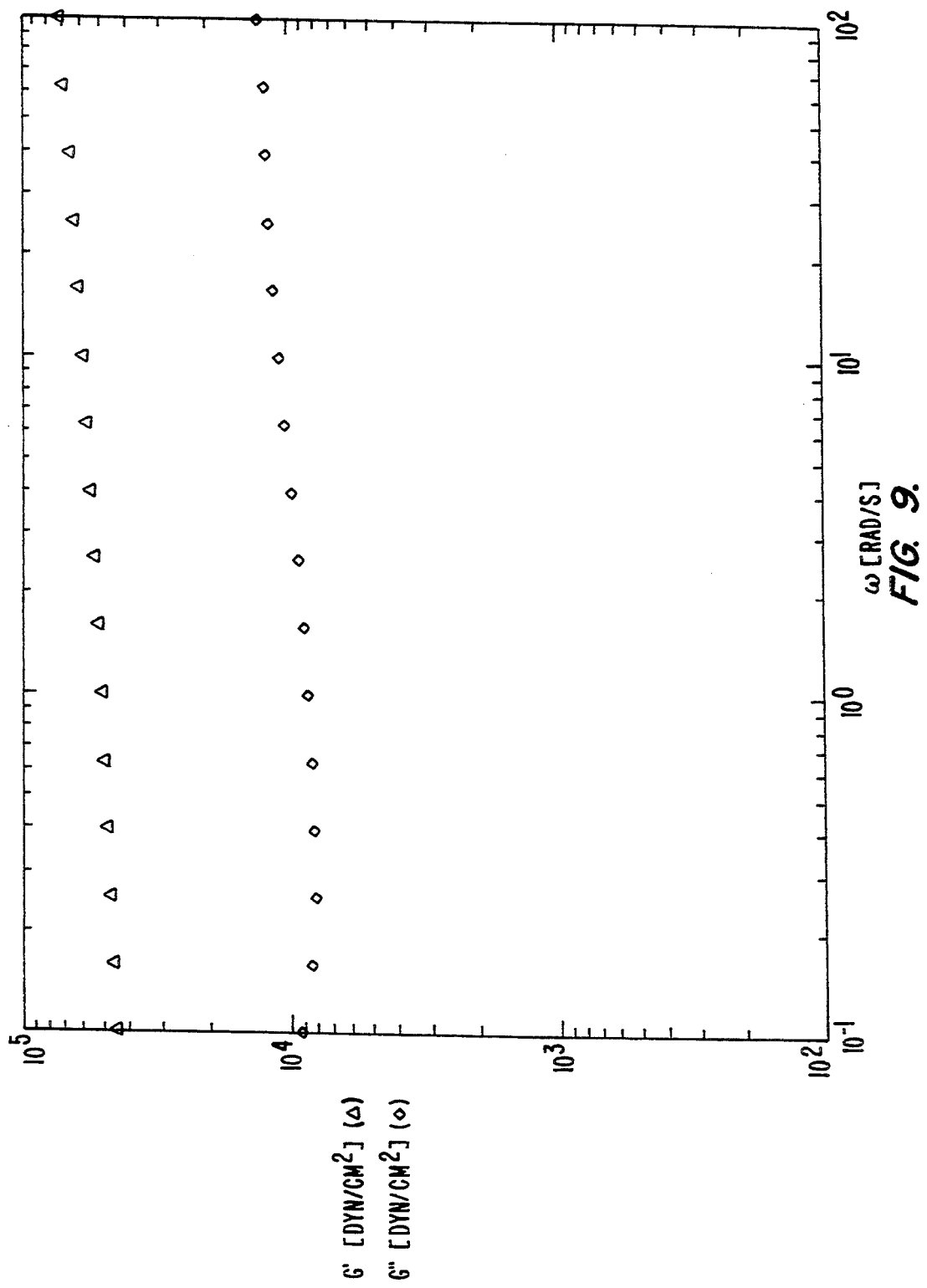
FIGS. 9-11 graphically illustrate frequency sweep measurements made on non-homogenized crosslinked and homogenized crosslinked materials described in the Experimental section hereinafter.
Figure 10:
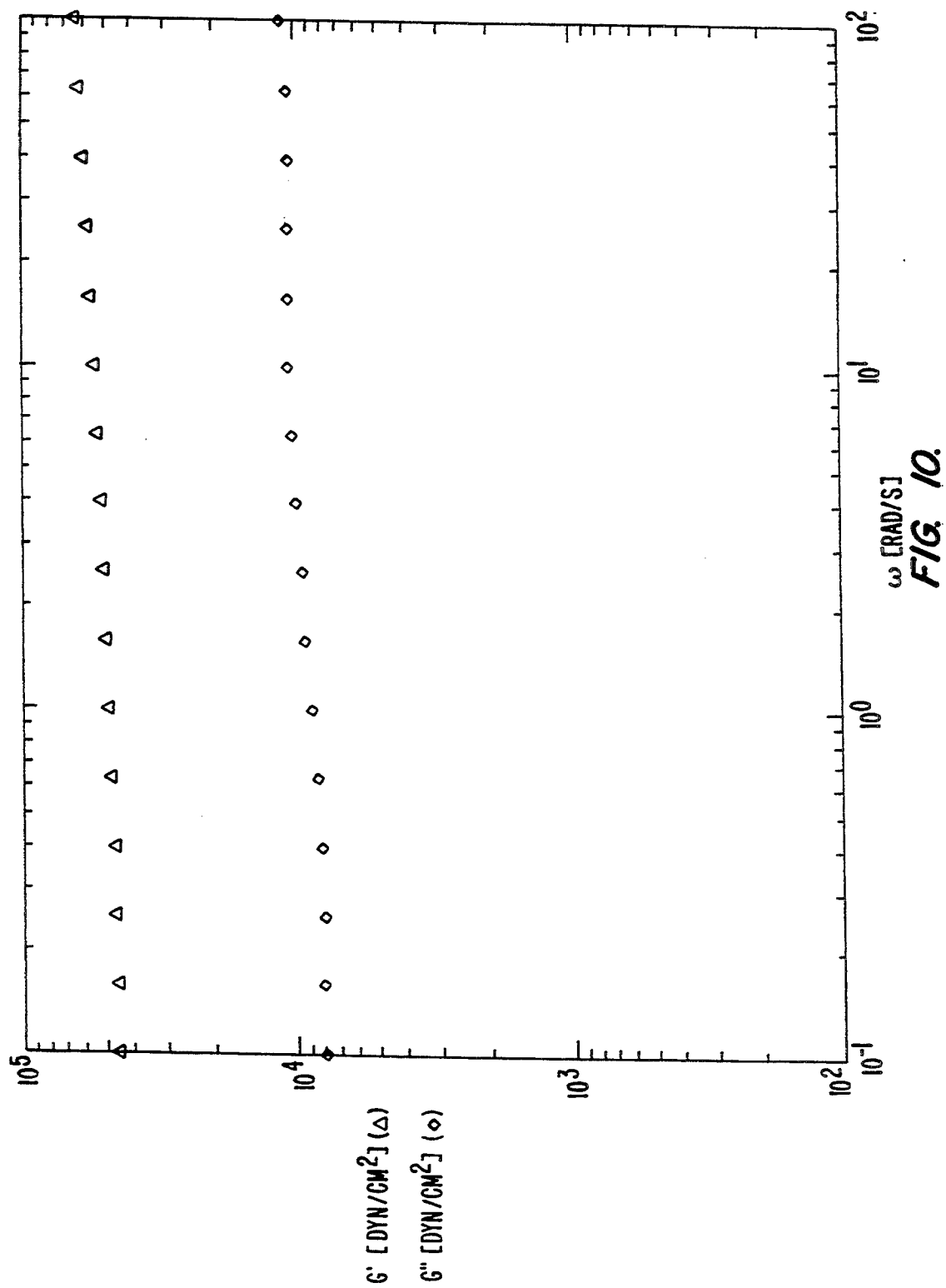
Figure 11:
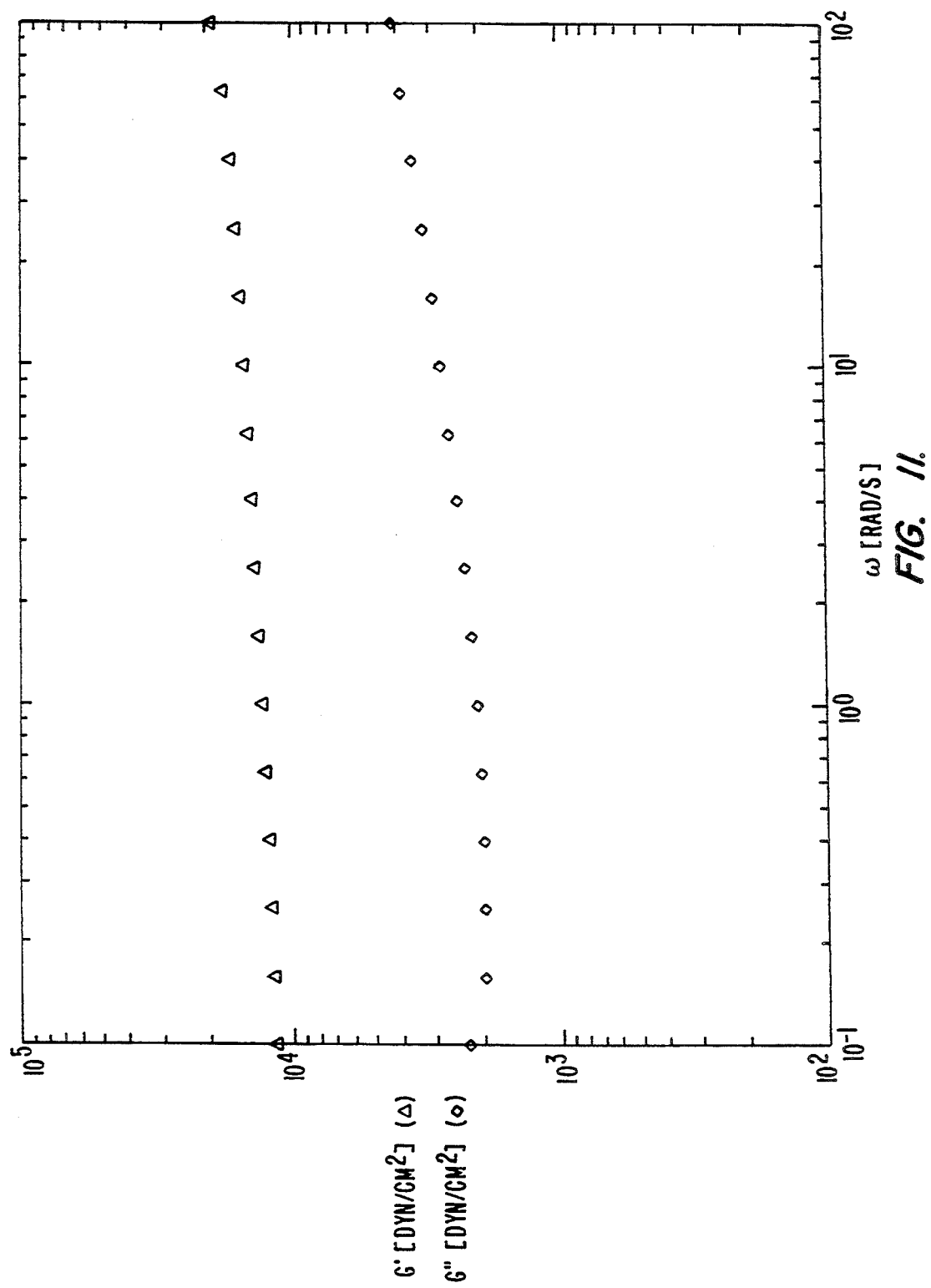
Figure 12:
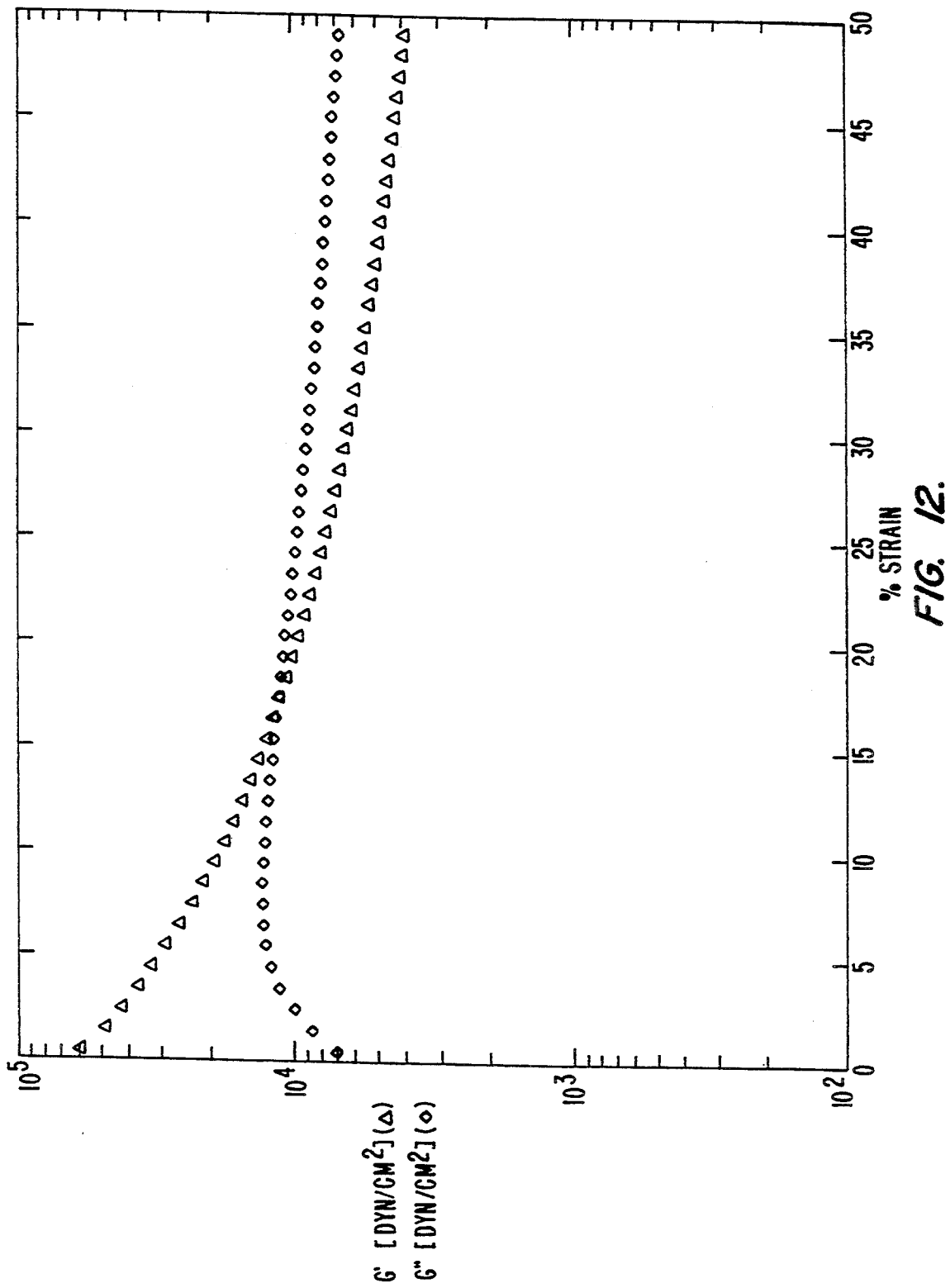
FIGS. 12-14 graphically illustrate strain sweep measurements made on crosslinked and homogenized crosslinked materials prepared as described in the Experimental section hereinafter.
Figure 13:
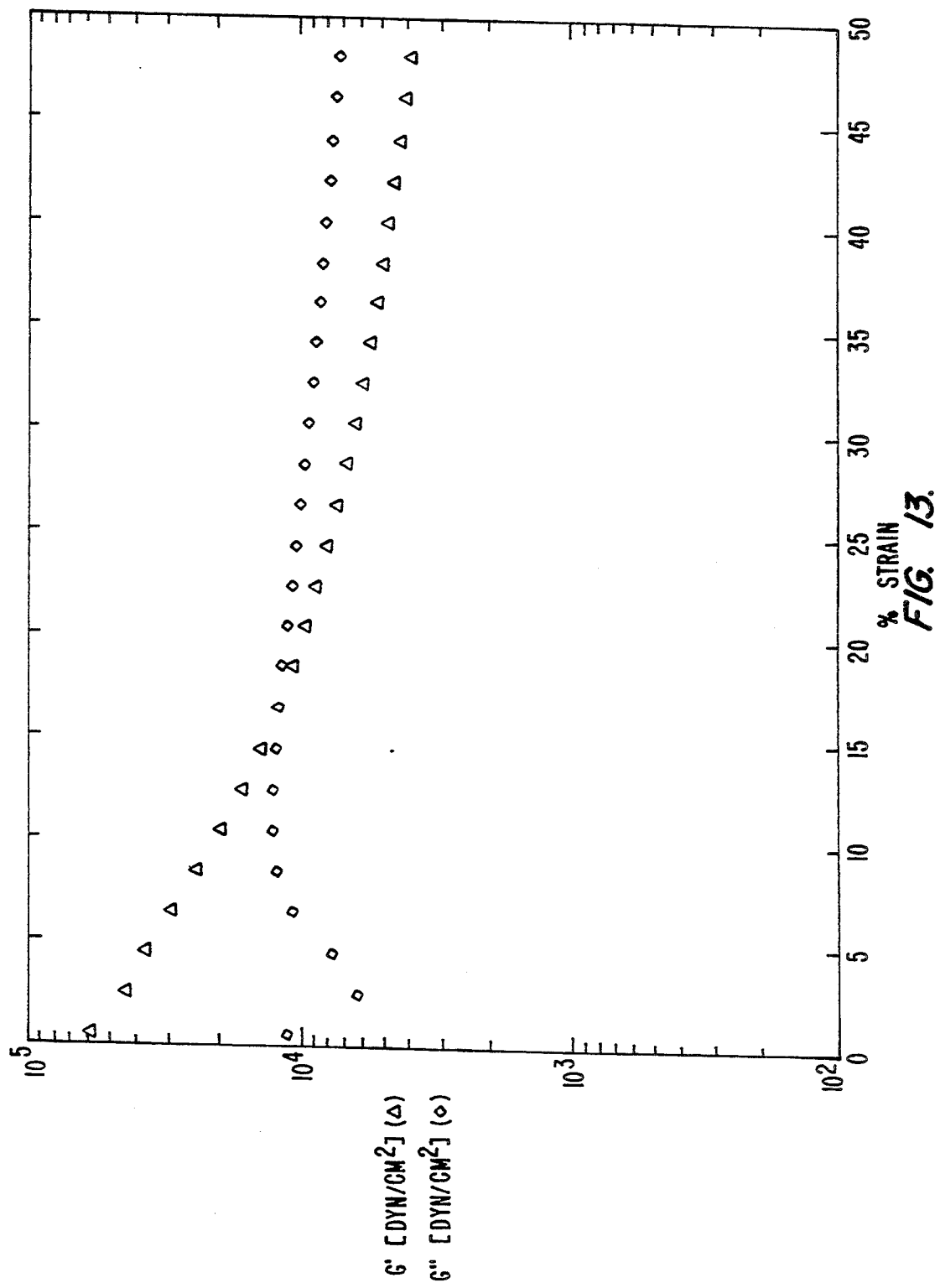
Figure 14:
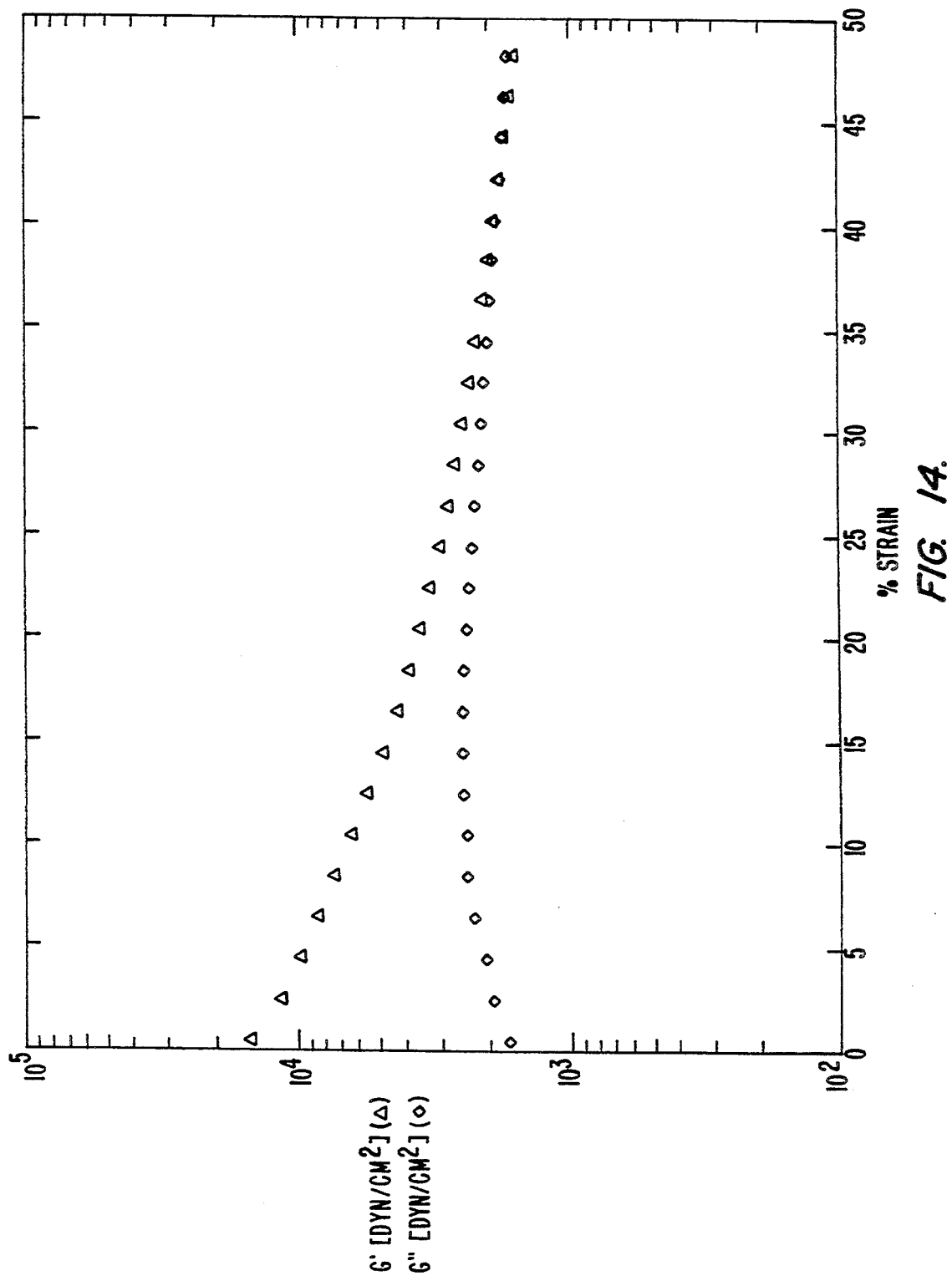
Figure 15:
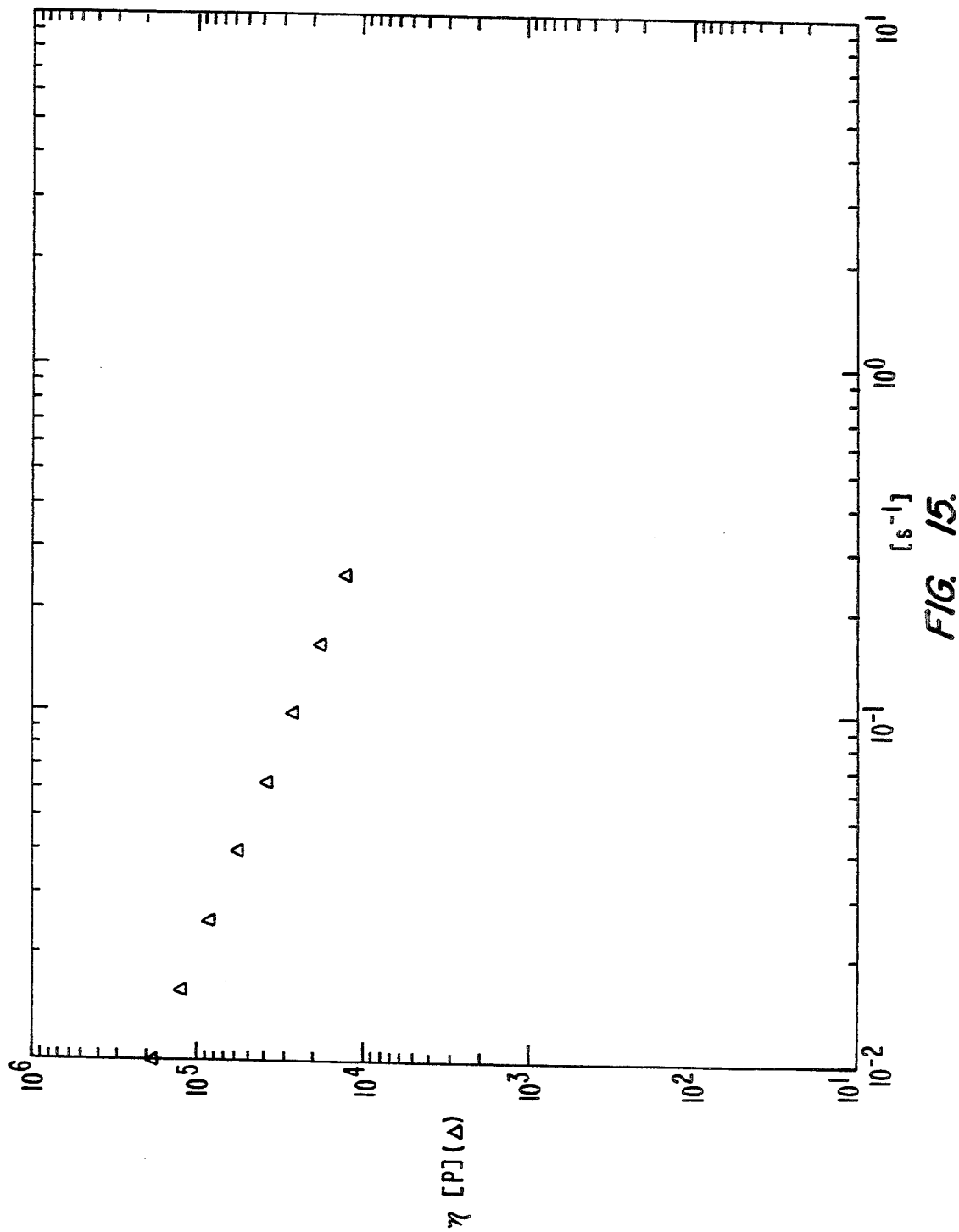
FIGS. 15 and 16 graphically illustrate shear viscosity ($\eta$) as a function of shear rate ($\gamma$) for crosslinked and homogenized crosslinked materials prepared as described in the Experimental section hereinafter.
Figure 16:
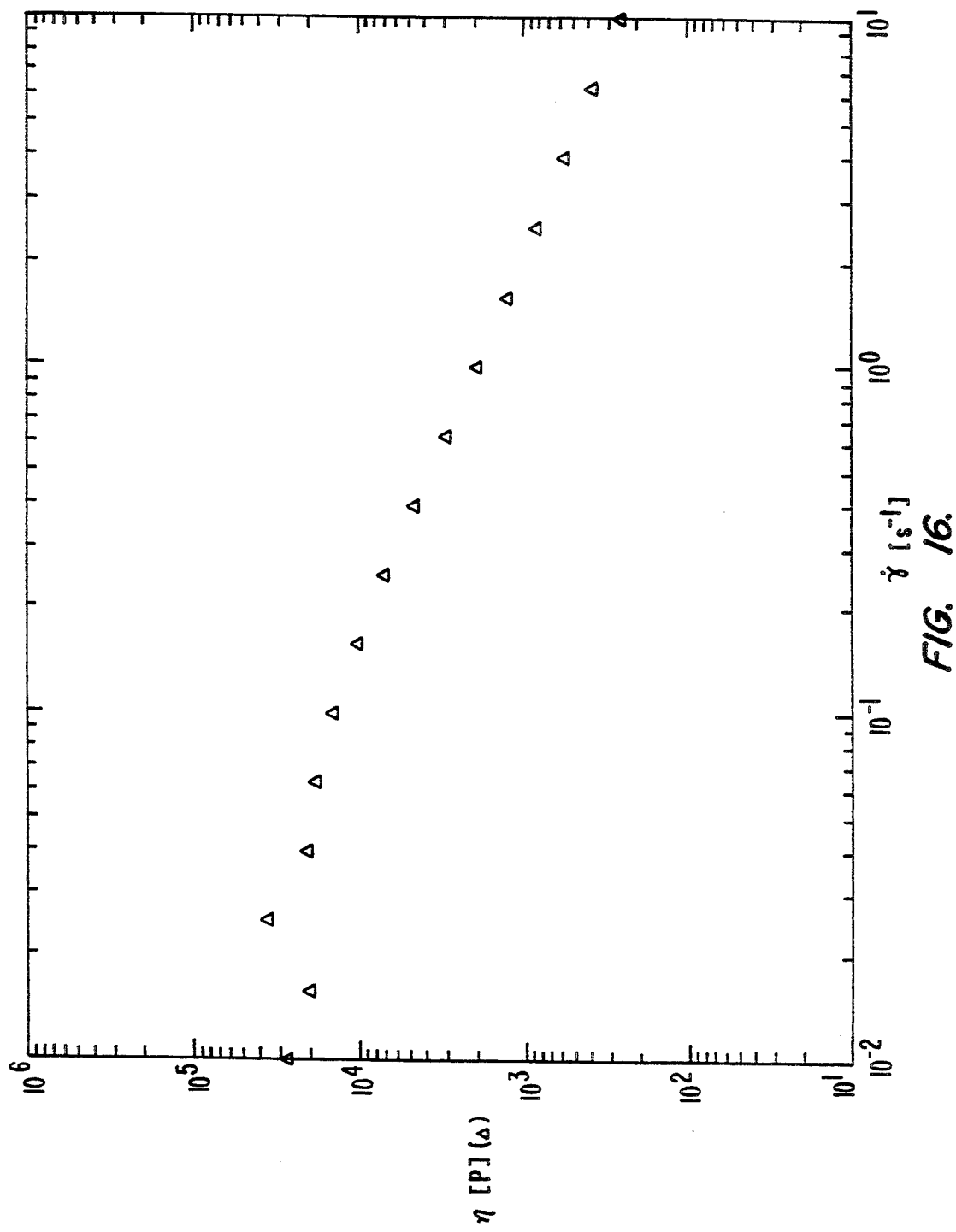

1. Frequency sweep at 1% strain (FIGS. 9, 10, 11).
2. Strain sweep from 0.5 to 50% strain at 1 rad/sec (FIGS. 12, 13, 14).
3. Steady shear viscosity versus shear rate (FIGS. 15 and 16).

The results of these tests are shown in FIG. 9 through 16.

The data indicate that the frequency and strain sweeps are similar for all three materials. The 65 mg/ml homogenized crosslinked collagen has higher moduli and viscosity values and is slightly more rigid than the 35 mg/ml non-homogenized crosslinked collagen. However, both the 65 mg/ml homogenized and 35 mg/ml non-homogenized collagens show very similar shear-thinning behavior. The strain sweeps indicate that the 65 mg/ml homogenized crosslinked collagen is not quite as homogeneous as the 35 mg/ml non-homogenized crosslinked collagen; however, the higher concentration material has slightly better flow properties.

D. Extrusion

Extrusion through a 30-gauge needle was measured for the 65 mg/ml homogenized crosslinked collagen and the 35 mg/ml non-homogenized crosslinked collagen. The samples of 65 mg/ml homogenized crosslinked collagen were transferred from 1.25 cc syringes to 1.0 cc syringes and further homogenized using syringe-syringe mixing (about ten passes) prior to performing the extrusion tests.

The 65 mg/ml non-homogenized crosslinked collagen could not be extruded through either a 27- or 30-gauge needle at speeds ranging from 10 to 100 mm/min. This material could be extruded through a larger needle (22-gauge); however, there were still plenty of spikes, indicating non-homogeneity.

Extrusion data for the 65 mg/ml homogenized crosslinked collagen and the 35 mg/ml non-homogenized crosslinked collagen are presented in Table VI.

TABLE VI

| | Force (Newtons) | |
|---|---|---|
| Speed (mm/min) | 65 mg/ml homogenized crosslinked collagen | 35 mg/ml non-homogenized crosslinked collagen |
| 10 | 16 | 4 |
| 30 | 18 | 5.5 |
| 50 | 21 | 6.8 |
| 100 | 26 | 9 |

Although the extrusion forces required for the 65 mg/ml homogenized crosslinked collagen were greater than those for the 35 mg/ml non-homogenized crosslinked collagen, they are still resonable and are, in fact, comparable to the extrusion forces presented in section 1(d) for the non-crosslinked collagens. The 65 mg/ml homogenized crosslinked collagen showed good extrusion plateaus with few spikes, suggesting fairly homogeneous material.

E. Capillary Rheometry

Capillary rheometry measurements were performed on 65 mg/ml homogenized crosslinked collagen and 35 mg/ml non-homogenized crosslinked collagen to compare changes in material structure and flow rate. The capillary rheometry technique consisted of performing extrusions at multiple speeds through long narrow-gauge needles on an Instron Analyzer. Viscosity/shear rate values are then calculated from the extrusion speed data. Viscosity/shear rate data are shown in Table VIII and FIG. 8.

TABLE VII

| Shear Rate (1/sec) | Viscosity (Pa-sec) |
|---|---|
| 65 mg/ml homogenized crosslinked collagen | |
| 29022.62 | 0.08423 |
| 65830.93 | 0.04341 |
| 73921.09 | 0.04178 |
| 147037.73 | 0.02702 |
| 35 mg/ml non-homogenized crosslinked collagen | |
| 15184.91 | 0.04025 |
| 41874.02 | 0.02007 |
| 64039.82 | 0.01622 |
| 128848.18 | 0.01067 |

F. Fiber Size Distribution

Fiber size distribution was measured for the following three materials by image analysis using an Olympus Cue-2 Image Analyzer.
1. 65 mg/ml non-homogenized crosslinked collagen.
2. 65 mg/ml homogenized crosslinked collagen.
3. 35 mg/ml non-homogenized crosslinked collagen.

Fiber size distribution data are presented in Table VIII.

TABLE VIII

| | Minimum to Maximum Object Area ($\mu m^2$) | Mean Object Area ($\mu m^2$) |
|---|---|---|
| 65 mg/ml crosslinked collagen | | |
| Non-homogenized | 34 to $2.45 \times 10^6$ | $64510 \pm 275571$ |
| Homogenized | 34 to $2.86 \times 10^5$ | $7154 \pm 26778$ |
| 35 mg/ml non-homogenized Crosslinked collagen | 34 to $4.09 \times 10^4$ | $997 \pm 2782$ |

The data indicate that homogenization causes the fiber size to decrease by a factor of almost nine. It also must be noted that the amount of variation in fiber size decreases following homogenization, indicating a more homogeneous material.

Although the foregoing invention has been described in detail for purposes of clarity of understanding, it will be obvious that certain modifications may be practiced within the scope of the appended claims.

What is claimed is:

1. A collagen composition comprising intrafibrillar cross-linked collagen particles suspended in a physiologically acceptable medium at a concentration greater than 50 mg/ml, wherein said cross-linked collagen particles have been sufficiently mechanically disrupted to reduce the average particle area by at least 25% when compared to non-disrupted particles.

2. A collagen composition as in claim 1 having rheological properties which permit injection through a 20 gauge needle.

3. A method for preparing high concentration, injectable collagen compositions, said method comprising:
    obtaining solubilized collagen from an animal source, said collagen comprising discrete collagen particles wherein the solubilized collagen is an aqueous suspension of cross-linked fibrillar collagen having a concentration greater than 50 mg/ml; and
    mechanically disrupting the cross-linked collagen particles in a homogenizer to reduce their average area by at least about 25%.

4. A method as in claim 3, wherein the particle area has been reduced by at least 50%.

5. A method for augmenting a tissue site in a living mammal, said method comprising injecting through a 20 gauge or smaller needle intrafibrillar cross-linked collagen particles present in a physiologically acceptable medium at a concentration greater than 50 mg/ml to the tissue site.

6. An improved collagen composition as in claim 1, wherein the mechanical disruption is sufficient to reduce particle area by at least 50%.

* * * * *